United States Patent
Wandner et al.

(10) Patent No.: US 11,680,164 B2
(45) Date of Patent: *Jun. 20, 2023

(54) BY MEANS OF IONIZING RADIATION STERILIZABLE MOULDED PARTS MADE FROM POLYCARBONATE

(71) Applicant: COVESTRO INTELLECTUAL PROPERTY GMBH & CO. KG, Leverkusen (DE)

(72) Inventors: Derk Erich Wandner, Odenthal (DE); Pierre Moulinie, Oakdale, PA (US); Ralf Hufen, Duisburg (DE)

(73) Assignee: Covestro Intellectual Property GmbH & Co. KG, Leverkusen (DE)

( * ) Notice: Subject to any disclaimer, the term of this patent is extended or adjusted under 35 U.S.C. 154(b) by 354 days.

This patent is subject to a terminal disclaimer.

(21) Appl. No.: 17/048,571

(22) PCT Filed: Apr. 12, 2019

(86) PCT No.: PCT/EP2019/059568
§ 371 (c)(1),
(2) Date: Oct. 16, 2020

(87) PCT Pub. No.: WO2019/201816
PCT Pub. Date: Oct. 24, 2019

(65) Prior Publication Data
US 2021/0179845 A1  Jun. 17, 2021

(30) Foreign Application Priority Data
Apr. 16, 2018 (EP) ..................... 18167430

(51) Int. Cl.
A61L 2/08 (2006.01)
C08L 69/00 (2006.01)
C08L 71/02 (2006.01)
C08K 5/372 (2006.01)
A61L 29/06 (2006.01)
A61L 29/14 (2006.01)

(52) U.S. Cl.
CPC .............. *C08L 69/00* (2013.01); *A61L 2/087* (2013.01); *A61L 29/06* (2013.01); *A61L 29/14* (2013.01); *C08K 5/372* (2013.01); *C08L 71/02* (2013.01); *A61L 2202/181* (2013.01); *A61L 2202/24* (2013.01); *C08L 2201/08* (2013.01)

(58) Field of Classification Search
None
See application file for complete search history.

(56) References Cited

U.S. PATENT DOCUMENTS

| | | |
|---|---|---|
| 2,991,273 A | 7/1961 | Hechelhammer et al. |
| 2,999,835 A | 9/1961 | Goldberg |
| 2,999,846 A | 9/1961 | Schnell et al. |
| 3,148,172 A | 9/1964 | Fox |
| 3,271,367 A | 9/1966 | Schnell et al. |
| 3,879,348 A | 4/1975 | Serini et al. |
| 4,982,014 A | 1/1991 | Freitag et al. |
| 5,097,002 A | 3/1992 | Sakashita et al. |
| 5,196,245 A * | 3/1993 | DeRudder ............. C08G 64/14 206/524.1 |
| 5,288,778 A | 2/1994 | Schmitter et al. |
| 5,340,905 A | 8/1994 | Kühling et al. |
| 5,717,057 A | 2/1998 | Sakashita et al. |
| 5,821,380 A | 10/1998 | Holderbaum et al. |
| 5,883,165 A | 3/1999 | Kröhnke et al. |
| 6,596,840 B1 | 7/2003 | Kratschmer et al. |
| 6,740,730 B1 | 5/2004 | Kratschmer et al. |
| 7,071,284 B2 | 7/2006 | Kauth et al. |
| 7,074,351 B2 | 7/2006 | Döbler et al. |
| 7,169,834 B2 | 1/2007 | Döbler et al. |
| 2021/0139697 A1* | 5/2021 | Wandner ................ A61L 2/087 |

FOREIGN PATENT DOCUMENTS

| | | |
|---|---|---|
| DE | 1570703 A1 | 2/1970 |
| DE | 2036052 A1 | 1/1972 |
| DE | 2063050 A1 | 7/1972 |
| DE | 2211956 A1 | 10/1973 |
| DE | 3832396 A1 | 2/1990 |
| DE | 10006208 A1 | 8/2001 |
| DE | 10022037 A1 | 11/2001 |
| EP | 0376289 A2 | 7/1990 |
| EP | 0500496 A1 | 8/1992 |
| EP | 0611797 A1 | 8/1994 |
| EP | 0839623 A1 | 5/1998 |
| EP | 1559743 A1 | 8/2005 |
| EP | 1865027 A1 | 12/2007 |
| EP | 2568004 A1 | 3/2013 |
| FR | 1561518 A | 3/1969 |
| GB | 1122003 A | 7/1968 |
| GB | 1229482 A | 4/1971 |

(Continued)

OTHER PUBLICATIONS

International Search Report for PCT/EP2019/059568 dated Jun. 17, 2019.

(Continued)

*Primary Examiner* — David J Buttner
(74) *Attorney, Agent, or Firm* — The Webb Law Firm

(57) ABSTRACT

The invention relates to a thermoplastic composition comprising A) aromatic polycarbonate, B) 0.1 to 5 wt.-% one or more polyether polyols and C) 0.01 to 0.30 wt.-% 3,3'-thiodipropionic acid. The invention also relates to medical technology products or parts of medical technology products consisting of such compositions as well as to a process for sterilization of such moulded parts by means of irradiation. The polycarbonate compositions according to the invention show significantly less yellowing after irradiation than known compositions and still have good mechanical properties.

14 Claims, No Drawings

(56) References Cited

FOREIGN PATENT DOCUMENTS

| | | | |
|---|---|---|---|
| GB | 1367790 A | | 9/1974 |
| JP | 2006249175 | * | 9/2006 |
| KR | 20150059666 A | | 6/2015 |
| WO | WO-9615102 A2 | | 5/1996 |
| WO | WO-0105867 A1 | | 1/2001 |
| WO | WO-200105866 A1 | | 1/2001 |
| WO | WO-2004063249 A1 | | 7/2004 |
| WO | WO-2019201815 A1 | | 10/2019 |

OTHER PUBLICATIONS

Written Opinion of the International Searching Authority for PCT/EP2019/059568 dated Jun. 17, 2019.
International Search Report for PCT/EP2019/059567 dated Jun. 13, 2019.
Written Opinion of the International Searching Authority for PCT/EP2019/059567 dated Jun. 13, 2019.

* cited by examiner

BY MEANS OF IONIZING RADIATION STERILIZABLE MOULDED PARTS MADE FROM POLYCARBONATE

CROSS-REFERENCE TO RELATED APPLICATIONS

This application is a national stage application (under 35 U.S.C. § 371) of PCT/EP2019/059568, filed Apr. 12, 2019, which claims benefit of European Application No. 18167430.0, filed Apr. 16, 2018, both of which are incorporated herein by reference in their entirety.

The present invention relates to compositions comprising aromatic polycarbonate and one or more polyether polyols, additionally comprising a new stabilizer. The invention also relates to medical technology products or parts of medical technology products comprising compositions according to the invention, as well as to a process for sterilization of a molded part produced from a respective composition.

Medical technology products, e.g. parts of dialyzers, have to be sterile for their use. This is not only the case for parts which are intended for multiple use, so-called MUD (multi-use medical devices), but also for parts for the single use, SUD (single use medical devices), as germs which can cause severe or even deadly infections are ubiquitous and are transported even via air.

Articles intended for medical use which shall be easily be available for use are usually delivered as sterile products, meaning that they have to undergo a sterilization process before being delivered packaged to the consumer so to keep up sterility. On point of use the respective packaging can be opened and the medical technology device can be used. A sterilization of unpackaged articles on site, e.g. in the same hospital, is not suitable for many products, as including a risk of contamination until final use.

Articles intended for single and for multiple use need to be sterilized in advance of their first appliance. This is usually done by means of ionizing radiation, in particular by means of β-radiation or γ-radiation, which is a very efficient way and does not require any additional steps, as, e.g., drying steps in the case of a sterilization process with a sterilization solution. Sterilization by means of radiation allows a sterilization of medical technology products in their closed packaging and thereby guarantees highest possible sterility. The articles remain sterile until opening of the packaging immediately before their use. Usually, radiation doses of 25 to 100 kGy are used, although even higher doses, at least up to 200 kGy are possible. Several articles can be sterilized at the same time.

One suitable material for medical technology products is polycarbonate material. The products made thereof are comparably cheap, easily producible by injection moulding or extrusion and can be given manifold forms. Polycarbonate materials are available in transparent, translucent and in opaque form. The material has a high breaking strength and high stiffness, high heat deflection temperature und good dimensional stability, which all makes it a well suited material for a lot of medical technology applications.

When articles made from compositions based on aromatic polycarbonate are irradiated, yellowing of the polycarbonate materials occurs, which is stronger with increasing radiation dose, which is due to degradation and rearrangement reactions. Already for usual radiation doses a significant yellowing of the material occurs.

There is also a high demand for conducting the radiation sterilization process in the absence of oxygen, which is particularly true for components such as (parts of) dialyzers.

The yellowing directly after irradiation partly recedes with relaxation of the sample. For the market it is interesting to have a rest colour as low as possible.

In order to keep any yellowing as low as possible, stabilizers are usually added to the polycarbonate material. As single stabilizers, e.g. polypropylene glycols, such as those described in EP 0 376 289 A2, do not lead to a sufficient stabilization against ionizing radiation, usually a stabilizer combination is used in order to achieve the best performance. Stabilizers in the form of polyether polyols are used, e.g. Multranol® 3600 DHP by Lanxess AG, Desmophen® 3600Z by Covestro Deutschland AG, polypropylene glycol Synalox 100 D95 by the Dow Chemical Company, additional stabilizers which are often used are sulfur-containing additives, e.g. disulfides described in EP 0 611 797 A1. However, there is a need for even more efficient stabilizer combinations. Other combinations, e.g. thioether stabilizers as pentaerythrityl tetrakis(3-laurylthiopropionate) together with an amide-based stabilizer as described in KR 20150059666 A still lead to too much increased Y.I. values after irradiation, so that further optimization is still necessary.

It was therefore an object of the present invention to provide even more efficient stabilizer combinations for stabilization of polycarbonate material which can be sterilized by irradiation. Furthermore, the resulting compositions should exhibit a good processability.

Surprisingly, it was found that 3,3'-thiodipropionic acid is a suitable stabilizer in combination with polyether polyols as stabilizers for polycarbonate-based compositions, and this under oxygen atmosphere and under oxygen-reduced atmosphere, up to oxygen-free atmosphere. 3,3'-Thiodipropionic acid, according to current market prices, is much cheaper than other already known stabilizers.

Subject-matter of the invention therefore is a thermoplastic composition comprising
  A) aromatic polycarbonate,
  B) 0.1 to 5 wt.-% one or more polyether polyols and
  C) 0.01 to 0.30 wt.-% 3,3'-thiodipropionic acid.

Weight indications in the context of the invention all refer to the overall composition, unless indicated otherwise.

The object of the invention is also achieved by a process for sterilization of a moulded part, wherein a moulded part consisting of or comprising an area consisting of a thermoplastic composition according to one of the preceding claims is exposed to β-radiation and/or γ-radiation with a dose of at least 20 kGy.

Thermoplastic compositions which are preferred according to the invention are those comprising
  A) 50 to 98.5 wt.-% aromatic polycarbonate,
  B) 0.1 to 2 wt.-% polyether polyol and
  C) 0.05 to 0.25 wt.-% 3,3'-thiodipropionic acid and
  D) further additives.

More preferred thermoplastic compositions consist of
  A) 69.85 wt.-% to 98.5 wt.-% aromatic polycarbonate,
  B) 0.1 wt.-% to 2 wt.-% polyether polyol and
  C) 0.05 wt.-% to 0.25 wt.-% 3,3'-thiodipropionic acid and
  D) up to 30 wt.-% one or more further additives selected from the group consisting of flame retardants, antidripping agents, impact modifiers, fillers, antistats, colouring agents, pigments, thermal stabilizers different from components B and C, lubricants and/or demoulding agents, UV absorbers, IR absorbers, hydrolysis stabilizers and/or compatibilizer.

Particularly preferred compositions consist of
  A) 93.0 wt.-% to 97.5 wt.-% aromatic polycarbonate,
  B) 0.5 wt.-% to 1 wt.-% polyether polyol and
  C) 0.05 wt.-% to 0.25 wt.-% 3,3'-thiodipropionic acid and D) up to 6 wt.-% one or more further additives selected from the group consisting of flame retardants, antidripping agents, impact modifiers, fillers, antistats, colouring agents, pigments, thermal stabilizers different from components B and C, lubricants and/or demoulding agents, UV absorbers, IR absorbers, hydrolysis stabilizers and/or compatibilizer.

Component A

According to the invention, "thermoplastic, aromatic polycarbonates" or else just "polycarbonates" is to be understood as encompassing both aromatic homopolycarbonates and copolycarbonates, including polyestercarbonates, wherein the polycarbonates may be linear or branched in familiar fashion. Also mixtures can be used.

A portion of up to 80 mol %, preferably of 20 mol % up to 50 mol %, of the carbonate groups in the polycarbonates used in accordance with the invention may be replaced by aromatic dicarboxylic ester groups. Polycarbonates of this kind, incorporating both acid radicals from the carbonic acid and acid radicals from aromatic dicarboxylic acids in the molecule chain, are referred to as aromatic polyestercarbonates. In the context of the present invention, they are encompassed by the umbrella term of the thermoplastic aromatic polycarbonates.

The replacement of the carbonate groups by aromatic dicarboxylic acid ester groups takes place essentially stoichiometrically and quantitatively, so that the molar ratio of the reaction partners can also be found in the finished polyestercarbonate. The incorporation of dicarboxylic acid ester groups can be statistical as well as in blocks.

The thermoplastic polycarbonates including the thermoplastic aromatic polyestercarbonates have weight average molecular weights $M_w$, determined by gel permeation chromatography under use of $CH_2Cl_2$ as diluent, of from 10,000 g/mol to 35,000 g/mol, preferably from 12,000 g/mol to 32,000 g/mol, more preferably from 15,000 g/mol to 32,000 g/mol, in particular from 20,000 g/mol to 31,500 g/mol, calibration with linear polycarbonate (made from bisphenol A and phosgene) of known molecular weight distribution, standards from PSS Polymer Standards Service GmbH, Germany, calibration according to method 2301-0257502-09D (from the year 2009 in German language) from Currenta GmbH & Co. OHG, Leverkusen. Diluent methylene chloride. Column combination from cross-linked styrenedivinylbenzene resin. Diameter of the analytical columns: 7.5 mm, length: 300 mm. Particle size of the column material: 3 m to 20 m. Concentration of the solutions: 0.2 wt.-%. Flow rate: 1.0 ml/min, temperature of the solution: 30° C. Detection by means of a refractive index (RI)-detector.

Particulars pertaining to the preparation of polycarbonates are disclosed in many patent documents spanning approximately the last 40 years. Reference may be made here to Schnell, "Chemistry and Physics of Polycarbonates", Polymer Reviews, Volume 9, Interscience Publishers, New York, London, Sydney 1964, to D. Freitag, U. Grigo, P. R. Miller, H. Nouvertné, BAYER AG, "Polycarbonates" in Encyclopedia of Polymer Science and Engineering, Volume 11, Second Edition, 1988, pages 648-718 and finally to U. Grigo, K. Kirchner and P. R. Müller "Polycarbonate" [Polycarbonates] in Becker/Braun, Kunststoff-Handbuch [Plastics Handbook], volume 3/1, Polycarbonate, Polyacetale, Polyester, Celluloseester [Polycarbonates, Polyacetals, Polyesters, Cellulose Esters], Carl Hanser Verlag Munich, Vienna 1992, pages 117-299.

Preferred processes for the production of the polycarbonates which are used according to the invention, including polyestercarbonates, are the interfacial process and the melt transesterification process (e.g. WO 2004/063249 A1, WO 2001/05866 A1, WO 2000/105867, U.S. Pat. Nos. 5,340,905 A, 5,097,002 A, 5,717,057 A).

Aromatic polycarbonates are prepared, for example, by reaction of dihydroxyaryl compounds with carbonyl halides, preferably phosgene, and/or with aromatic dicarbonyl dihalides, preferably benzenedicarbonyl dihalides, by the interfacial process, optionally with use of chain terminators and optionally with use of trifunctional or more than trifunctional branching agents, wherein for the production of polyestercarbonates a part of the carbonic acid derivatives is replaced with aromatic dicarboxylic acids or derivatives of dicarboxylic acids, namely according to the carbonate structure units in the aromatic polycarbonates by dicarboxylic acid ester structure units. Preparation via a melt polymerization process by reaction of dihydroxyaryl compounds with, for example, diphenyl carbonate is likewise possible.

Dihydroxyaryl compounds suitable for the preparation of polycarbonates are those of the formula (1)

$$HO-Z-OH \quad (1),$$

in which

Z is an aromatic radical which has 6 to 30 carbon atoms and may contain one or more aromatic rings, may be substituted and may contain aliphatic or cycloaliphatic radicals or alkylaryls or heteroatoms as bridging elements.

Preferably, Z in formula (1) is a radical of the formula (2)

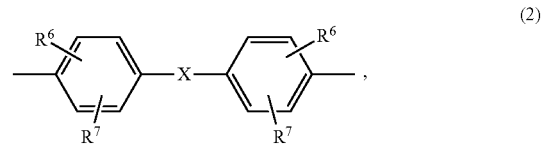

(2)

in which $R^6$ and $R^7$ are each independently H, $C_1$- to $C_{18}$-alkyl-, $C_1$- to $C_{18}$-alkoxy, halogen such as Cl or Br or in each case optionally substituted aryl or aralkyl, preferably H or $C_1$- to $C_{12}$-alkyl, more preferably H or $C_1$- to $C_8$-alkyl and most preferably H or methyl, and X is a single bond, $-SO_2-$, $-CO-$, $-O-$, $-S-$, $C_1$- to $C_6$-alkylene, $C_2$- to $C_5$-alkylidene or $C_5$- to $C_6$-cycloalkylidene which may be substituted by $C_1$- to $C_6$-alkyl, preferably methyl or ethyl, or else $C_6$- to $C_{12}$-arylene which may optionally be fused to further aromatic rings containing heteroatoms.

Preferably, X is a single bond, $C_1$- to $C_5$-alkylene, $C_2$- to $C_5$-alkylidene, $C_5$- to $C_6$-cycloalkylidene, $-O-$, $-SO-$, $-CO-$, $-S-$, $-SO_2-$ or a radical of the formula (2a)

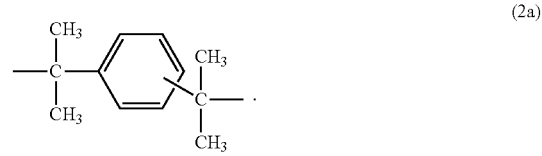

(2a)

Examples of dihydroxyaryl compounds suitable for the preparation of the polycarbonates for use in accordance with the invention include hydroquinone, resorcinol, dihydroxydiphenyl, bis(hydroxyphenyl)alkanes, bis(hydroxyphenyl) cycloalkanes, bis(hydroxyphenyl) sulphides, bis(hydroxyphenyl) ethers, bis(hydroxyphenyl) ketones, bis (hydroxyphenyl) sulphones, bis(hydroxyphenyl) sulphoxides, α,α'-bis(hydroxyphenyl)diisopropylbenzenes and the alkylated, ring-alkylated and ring-halogenated compounds thereof.

Preferred dihydroxyaryl compounds are 4,4'-dihydroxydiphenyl, 2,2-bis(4-hydroxyphenyl)propane (bisphenol A), 2,4-bis(4-hydroxyphenyl)-2-methylbutane, dimethyl-bisphenol A, 1,1-bis(4-hydroxyphenyl)-p-diisopropylbenzene, 2,2-bis(3-methyl-4-hydroxyphenyl)propane, 2,2-bis(3-methyl-4-hydroxyphenyl)propane, bis(3,5-dimethyl-4-hydroxyphenyl)methane, 2,2-bis(3,5-dimethyl-4-hydroxyphenyl)propane, bis(3,5-dimethyl-4-hydroxyphenyl)sulfone, 2,4-bis(3,5-dimethyl-4-hydroxyphenyl)-2-methylbutane, 1,1-bis(3,5-dimethyl-4-hydroxyphenyl)-p-diisopropylbenzene and 1,1-bis(4-hydroxyphenyl)-3,3,5-trimethylcyclohexane, and bisphenols (I) to (III)

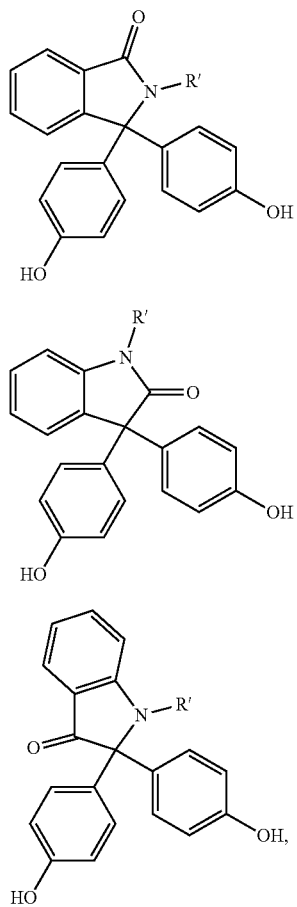

in which R' in each case is $C_1$- to $C_4$-alkyl, aralkyl or aryl, preferably methyl or phenyl, most preferably methyl.

Particularly preferred dihydroxyaryl compounds are 2,2-bis-(4-hydroxyphenyl)-propane (bisphenol A), 2,2-bis(3,5-dimethyl-4-hydroxyphenyl)propane, 1,1-bis(4-hydroxyphenyl)cyclohexane and 1,1-bis(4-hydroxyphenyl)-3,3,5-trimethylcyclohexane (bisphenol TMC) and dimethyl-bisphenol A as well as the dihydroxyaryl compounds of formula (I), (II) and (III).

These and further suitable dihydroxyaryl compounds are described, for example, in U.S. Pat. Nos. 2,999,835 A, 3,148,172 A, 2,991,273 A, 3,271,367 A, 4,982,014 A and 2,999,846 A, in German published specifications 1 570 703 A, 2 063 050 A, 2 036 052 A, 2 211 956 A and 3 832 396 A, in French patent application 1 561 518 A1, in the monograph "H. Schnell, Chemistry and Physics of Polycarbonates, Interscience Publishers, New York 1964, p. 28 ff.; p. 102 ff", and in "D. G. Legrand, J. T. Bendler, Handbook of Polycarbonate Science and Technology, Marcel Dekker New York 2000, p. 72ff.".

Only one dihydroxyaryl compound is used in the case of the homopolycarbonates; two or more dihydroxyaryl compounds are used in the case of copolycarbonates. The dihydroxyaryl compounds employed—as well as components of the compositions according to the invention-, similarly to all other chemicals and assistants added to the synthesis, may be contaminated with the contaminants from their own synthesis, handling and storage. However, it is desirable to employ the purest possible raw materials.

Examples of suitable carbonic acid derivatives include phosgene or diphenyl carbonate.

Suitable chain terminators that may be used in the production of polycarbonates are monophenols. Suitable monophenols are for example phenol itself, alkylphenols such as cresols, p-tert-butylphenol, cumylphenol and mixtures thereof.

Preferred chain terminators are the phenols mono- or polysubstituted by linear or branched $C_1$- to $C_{30}$-alkyl radicals, preferably unsubstituted or substituted by tert-butyl. Particularly preferred chain terminators are phenol, cumylphenol and/or p-tert-butylphenol.

The amount of chain terminator to be used is preferably 0.1 to 5 mol %, based on moles of dihydroxyaryl compounds used in each case. The chain terminators can be added before, during or after the reaction with a carbonic acid derivative.

Suitable branching agents are the trifunctional or more than trifunctional compounds familiar in polycarbonate chemistry, in particular those having three or more than three phenolic OH groups.

Examples of suitable branching agents include 1,3,5-tri(4-hydroxyphenyl)benzene, 1,1,1-tri(4-hydroxyphenyl)ethane, tri(4-hydroxyphenyl)phenylmethane, 2,4-bis(4-hydroxyphenylisopropyl)phenol, 2,6-bis(2-hydroxy-5'-methylbenzyl)-4-methylphenol, 2-(4-hydroxyphenyl)-2-(2,4-dihydroxyphenyl)propane, tetra(4-hydroxyphenyl)methane, tetra(4-(4-hydroxyphenylisopropyl)phenoxy)methane and 1,4-bis((4',4"-dihydroxytriphenyl)methyl)benzene and 3,3-bis(3-methyl-4-hydroxyphenyl)-2-oxo-2,3-dihydroindole.

The amount of any branching agents to be used is 0.05 mol % to 2 mol %, again based on moles of dihydroxy aryl compounds used in each case.

The branching agents can either be initially charged together with the dihydroxyaryl compounds and the chain terminators in the aqueous alkaline phase or added dissolved in an organic solvent before the phosgenation. In the case of the transesterification process the branching agents are used together with the dihydroxyaryl compounds.

Particularly preferred polycarbonates are the homopolycarbonate based on bisphenol A, the homopolycarbonate based on 1,3-bis(4-hydroxyphenyl)-3,3,5-trimethylcyclohexane and the copolycarbonates based on the two monomers bisphenol A and 1,1-bis(4-hydroxyphenyl)-3,3,5-trimethylcyclohexane, and homo- or copolycarbonates derived from the dihydroxyaryl compounds of the formulae (I) to (III)

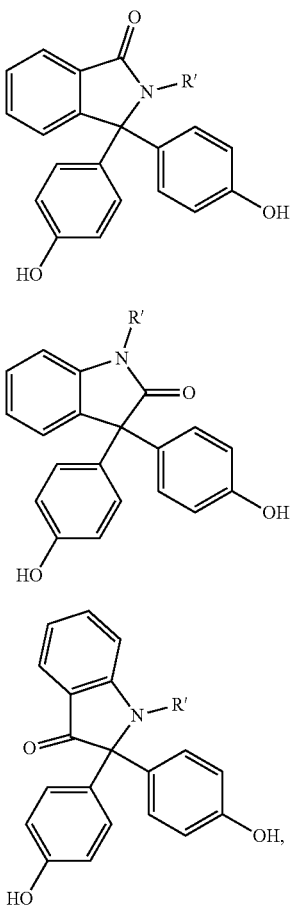

in which R' in each case is $C_1$- to $C_4$-alkyl, aralkyl or aryl, preferably methyl or phenyl, most preferably methyl, preferably with bisphenol A as comonomer.

To facilitate incorporation of additives, component A is preferably employed in the form of powders, pellets or mixtures of powders and pellets.

The polycarbonate preferably has an MVR of from 5 to 20 cm³/(10 min), more preferably of from 5.5 to 12 cm³/(10 min), even more preferably of from 6 to 10 cm³/(10 min), determined according to ISO 1133:2012-03 at a test temperature of 300° C. and 1.2 kg load.

A mixture of different polycarbonates can be used as polycarbonate, for example a mixture of the polycarbonates A1 and A2, wherein A2 is a polycarbonate in powdered form. The preferred properties for the polycarbonate refer to a respective mixture.

The compositions according to the invention preferably contain 50 to 98.5 wt.-%, more preferably 69.85 to 98.0 wt.-%, even more preferably 85 to 97.5 wt.-%, particularly preferably 90.0 to 97.5 wt.-%, in particular 93.0 wt.-% to 97.5 wt.-% aromatic polycarbonate.

Component B

Component B are stabilizers in the form of polyether polyols.

Polyether polyols are usually the product of the polymerization of epoxides, such as ethylene oxide (EO), propylene oxide (PO), butylene oxide, styrene oxide or epichlorhydrin, with themselves or by addition of such epoxides, optionally in admixture or sequentially, to starting components with reactive hydrogen atoms, such as water, alcohol, ammonia or amines. Such "starter molecules" usually have a functionality of from 1 to 6. Depending on the process control, such polyether polyols may be homopolymers, block copolymers, random copolymers, capped polymers or polymers tipped with a mixture of different epoxides. To specify such polyether polyols, various characteristics have become established in the prior art:

i) hydroxyl functionality, which depends on the starter molecule starting from which the polyether polyol is synthesized;

ii) hydroxyl or OH number, which is a measure of the content of hydroxyl groups stated in mg of KOH/g, determined according to DIN 53240-3:2016-03;

iii) when epoxides in which the ring opening causes the formation of different, i.e. primary or secondary) hydroxyl groups are used, on the one hand, the proportion of the respective epoxides in the polyether polyol is stated, and on the other hand, the proportion of primary or secondary hydroxyl groups based on the total number of hydroxyl groups present in the polyether polyol is stated;

iv) the molecular weight ($M_n$ or $M_w$), which is a measure of the length of the polyoxyalkylene chains of the polyether polyols.

The polyether polyols preferably have a number average molecular weight $M_n$ of from 100 to 6200 g/mol, more preferably 1500 to 4000 g/mol, even more preferably 1800 to 3000 g/mol. $M_n$ ist calculated according to the following formula: $M_n = 56100*F/OHN$. OH-number (OHN) is determined via hydroxyl end group titration as per DIN 53240-3:2016-03. OHN in mg KOH/g is inserted in the given formula. F is the functionality, which in the context of this invention related to hydroxyl end groups. Acid end groups, if any, are not taken into account. F is defined as number of hydroxyl end groups, divided by the number of molecules in an ensemble, meaning F is the average number of hydroxyl end groups of a molecule of a compound. F is normally apparent from the recipe for preparing the polyol, but may alternatively be determined by $^1$H NMR.

The polyether polyols can be formed from repeating ethylene oxide and propylene oxide units, e.g. with a share of 35 to 100 wt.-% propylene oxide units, particularly preferably 50 to 100 wt.-% propylene oxide units. The copolymers can be statistical copolymers, gradient copolymers, alternating copolymers or block copolymers formed from ethylene oxide and propylene oxide. Preferably, the polyether polyols are linear polymers.

However, preferred polyether polyols are those just formed from repeating propylene oxide units with a 1,2-diol as starter molecule, more preferably with propylene glycol as starter molecule. The polyether polyols can be end-capped or not end-capped. Preferably, the polyether polyol is end-capped. A preferred agent for end-capping is dihydropyran (3,4-dihydro-2H-pyran).

Suitable polyether polyols, formed from repeating propylene oxide and/or ethylene oxide units are, e.g., Desmophen®-, Acclaim®-, Arcol®-, Baycoll®-, Bayfill®-, Bayflex®-Baygal®-, PET®-polyetherpolyols from Covestro AG (for example Desmophen® 3600Z, Desmophen® 1900U, Acclaim® Polyol 2200, Acclaim® Polyol 40001, Arcol® Polyol 1004, Arcol® Polyol 1010, Arcol® Polyol 1030, Arcol® Polyol 1070, Baycoll® BD 1110, Bayfill® VPPU 0789, Baygal® K55, PET® 1004, Polyether® S180). Further suitable homo-polyethylene oxides are, for example, the Pluriol® E-range from BASF SE. Suitable homo-propylene oxides are, for example, the Pluriol® P-range from BASF SE or Multranol®-types from Lanxess AG, the Synalox-range of The Dow Chemical Company and the Caradol-range of Shell Chemicals. Suitable mixed copolymers formed from ethylene oxide and propylene oxide are, for example, the Pluronic® PE or Pluriol® RPE-ranges from BASF SE.

Particularly preferred polyether polyols are those formed from repeating propylene oxide units with propylene glycol as starter molecule, an OH number within a range of from 50 to 70 mg KOH/g determined according to DIN 53240-3:2016-03, and having a hydroxyl functionality of 2, a proportion of primary hydroxyl groups within a range of from 0 to 3%, based on the total number of primary and secondary hydroxyl groups, having a propylene oxide content of at least 95 wt.-% and ethylene oxide content of up to 3 wt.-%, very particularly preferred those without any ethylene oxide units, but just with propylene oxide units.

The compositions according to the invention comprise polyether polyols in an amount of from 0.1 to 5 wt.-%, preferably 0.1 to 2 wt.-%, more preferably 0.5 to 1 wt.-%, in particular 0.5 to 1.0 wt.-%, all amounts referring to the overall composition.

Component C

Component C of the compositions according to the invention is 3,3'-thiodipropionic acid. According to the invention, 3,3'-thiodipropionic acid is added in amounts of 0.01 to 0.30 wt.-%, preferably 0.05 to 0.25 wt.-%, more preferably 0.1 bis 0.25 wt.-%, referring to the overall composition. The purity of the 3,3'-thiodipropionic acid preferably is >99 wt.-%.

In one embodiment, the composition according to the invention does not contain any amino group-bearing substances. In another embodiment, the composition according to the invention does not contain any esters of thiodicarboxylic acids, in particular any esters of 3,3'-thiodipropionic acid. In another embodiment, the composition according to the invention contains neither amino group-bearing substances nor any esters of thiodicarboxylic acids, in particular any esters of 3,3'-thiodipropionic acid.

Component D

The compositions according to the invention may comprise other conventional additives ("further additives"). This group includes flame retardants, antidripping agents, impact modifiers, fillers, antistats, colouring agents, pigments, thermal stabilizers different from components B and C, lubricants and/or demoulding agents, UV absorbers, IR absorbers, hydrolysis stabilizers and/or compatibilizers.

Such additives as typically added in the case of polycarbonates are described, for example, in EP 0 839 623 A1, WO 96/15102 A2, EP 0 500 496 A1 or "Plastics Additives Handbook", Hans Zweifel, 5th Edition 2000, Hanser Verlag, Munich.

The group of further additives does not include 3,3'-thiodipropionic acid, as this is mentioned as component C. Furthermore, the group of component D does not include polyether polyols, as these are mentioned as component B.

The amount of further additives preferably is up to 30 wt.-%, more preferably up to 10 wt.-%, even more preferably up to 6 wt.-%, particularly preferably 0.01 to 3 wt.-%, in particular 1 wt.-%, all values referring to the overall composition and all including the upper value.

Preferred demoulding agents are pentaerythrityl tetrastearate (PETS) or glycerine monostearate (GMS), their carbonates and/or mixture of these demoulding agents.

Preferably, up to 0.1 wt.-%, more preferably 0.0001 wt.-% to 0.001 wt.-%, even more preferably 0.0004 wt.-% to 0.001 wt.-%, one or more colouring agents are contained as additive. The amount "to 0.001 wt.-% of one or more colouring agents" means that up to 0.001 wt.-% (inclusive) of colouring agents in total are included. If it is a mixture of two or more colouring agents, the upper limit for the mixture of colouring agents is 0.001 wt.-%. Colouring agents may be used to improve the visual impression if it is intended to even compensate a minimum rest discoloration after irradiation, if present. It is however also possible to use compositions without any colouring agents. It is also possible to use even more colouring agents.

Colouring agents or pigments in the sense of the present invention according to component D are, e.g. sulfur-containing pigments as Cadmium red or Cadmium yellow, iron cyanide-based pigments as Prussian Blue, oxide pigments as titan dioxide, zinc oxide, red iron oxide, black iron oxide, chromium oxide, titanium yellow, zinc-iron-based brown, titan-cobalt-based green, cobalt blue, copper-chromium-based black, copper-iron-based black or chromium-based pigments as chromium yellow, phthalocyanine-based colouring agents as copper-phthalocyanine blue or copper-phthalocyanine green, condensed polycyclic colouring agents and pigments as azo-based ones (for example nickel-azo-yellow), sulfur-indigo colouring agents, perinone-based, perylene-based, quinacridone-based, dioxazine-based, isoindolinone-based and quinophthalone-based derivatives, anthraquinone-based, heterocyclic systems.

Specific examples for colouring agents are the commercial products MACROLEX® Blue RR, MACROLEX® Violet 3R, MACROLEX® EG, MACROLEX® Violet B (Lanxess AG, Deutschland), Sumiplast® Violet RR, Sumiplast® Violet B, Sumiplast® Blue OR, (Sumitomo Chemical Co., Ltd.), Diaresin® Violet D, Diaresin® Blue G, Diaresin® Blue N (Mitsubishi Chemical Corporation), Heliogen® Blue or Heliogen® Green (BASF AG, Deutschland). Further suitable colouring agents are, e.g., Amaplast Yellow GHS (CAS 13676-91-0; Solvent Yellow 163; C.I. 58840); Keyplast Blue KR (CAS 116-75-6; Solvent Blue 104; C.I. 61568), Heliogen Blue types (e.g. Heliogen Blue K 6911; CAS 147-14-8; Pigment Blue 15:1; C.I. 74160) as well as Heliogen Green types (as e.g. Heliogen Green K 8730; CAS 1328-53-6; Pigment Green 7; C.I. 74260).

Cyanine-, quinolone-, anthraquinone-, phthalocyanine-derivatives are particularly preferred.

Suitable pigments are titan dioxide, talc, wollastonite and/or mica. Even carbon black might be a suitable pigment, although, if carbon black is used, the amount preferably is very low, i.e. only up to <0.1 wt.-%, to avoid any effect of colouring by carbon black.

In a particularly preferred embodiment according to the present invention, compositions are used which contain blue and/or violet colouring agents. This partly compensates the visual yellow colour impression which is a consequence of damage by irradiation. In combination with the stabilizer combination according to the invention, this gives the least coloured ready-to-use articles.

Optionally, the composition comprises an UV absorber. Preferred UV absorbers are those having as low a transmission as possible below 400 nm and as high a transmission as possible above 400 nm. Such UV absorbers are known and for example described in EP 0 839 623 A1, WO 1996/15102 A2 and EP 0 500 496 A1. Ultraviolet absorbers particularly suitable for use in the composition according to the invention are benzotriazoles, triazines, benzophenones and/or arylated cyanoacrylates.

Particularly suitable ultraviolet absorbers are hydroxy-benzotriazoles, such as 2-(3',5'-bis(1,1-dimethylbenzyl)-2'-hydroxyphenyl)benzotriazole (Tinuvin® 234, BASF, Ludwigshafen), 2-(2'-hydroxy-5'-(tert-octyl)phenyl) benzotriazole (Tinuvin® 329, BASF, Ludwigshafen), bis(3-(2H-benzotriazolyl)-2-hydroxy-5-tert-octyl)methane (Tinuvin® 360, BASF, Ludwigshafen), 2-(4,6-diphenyl-1,3,5-triazin-2-yl)-5-(hexyloxy)phenol (Tinuvin® 1577, BASF, Ludwigshafen), and also benzophenones such as 2,4-dihydroxybenzophenone (Chimassorb® 22, BASF, Ludwigshafen) and 2-hydroxy-4-(octyloxy)benzophenone (Chimassorb® 81, BASF, Ludwigshafen), 2,2-bis[[(2-cyano-1-oxo-3,3-diphenyl-2-propenyl)oxy]methyl]-1,3-propanediyl ester (9CI) (Uvinul® 3030, BASF AG Ludwigshafen), 2-[2-hydroxy-4-(2-ethylhexyl)oxy]phenyl-4,6-di(4-phenyl)phenyl-1,3,5-triazine (Tinuvin® 1600, BASF, Ludwigshafen), tetraethyl-2,2'-(1,4-phenylenedimethylidene) bismalonate (Hostavin® B-Cap, Clariant AG) or N-(2-ethoxyphenyl)-N'-(2-ethylphenyl)ethanediamide (Tinuvin® 312, CAS No. 23949-66-8, BASF, Ludwigshafen).

Particularly preferred specific UV absorbers are Tinuvin® 360, Tinuvin® 329 and/or Tinuvin® 312, very particular preference being given to Tinuvin® 329 and Tinuvin® 312.

It is also possible to employ mixtures of these ultraviolet absorbers.

Suitable IR absorbers are described, e.g. in EP 1 559 743 A1, EP 1 865 027 A1, DE 10 022 037 A1 and DE 10 006 208 A1. Of those mentioned in the literature, boride- and/or tungstate-based IR absorbers, in particular caesium tungstate or zinc-doped caesium tungstate, as well as ITO- or ATO-based IR absorbers and combinations thereof are particularly preferred.

Suitable impact modifiers are core-shell type impact modifiers, e.g. ABS, MBS, acryl-based, silicone-acryl-based impact modifiers, as well as non-core-shell type impact modifiers.

The polycarbonate compositions according to the invention may comprise organic and/or inorganic fillers in the usual amounts.

Suitable fillers are, e.g. chalk, quartz powder, titanium dioxide, silicates, aluminosilicates, e.g. talc, wollastonite, montmorillonite, also modified by ion exchange, kaolin, zeolite, vermiculite, aluminium oxide and/or silica. Mixture of these or these and other fillers can also be used.

Polytetrafluoroethylene is used as preferred antidripping agent.

Other sulfur-containing stabilizers can be used in addition to 3,3'-thiodipropionic e.g. distearyl disulfide (Hostanox SE 10 of Clariant AG), pentaerythrityl tetrakis(3-laurylthiopropionate) (SOGNOX® 4120 of Songwon International AG) and/or bis-(phenylsulfonyl)methane.

The polymer compositions according to the invention, comprising components A to C and optionally D, are produced by standard incorporation processes via combination, mixing and homogenization of the individual constituents, especially with the homogenization preferably taking place in the melt under the action of shear forces. If appropriate, combination and mixing prior to the melt homogenization is effected using powder premixes.

For all components used it is desirable to employ the purest possible compounds.

It is also possible to use premixes of granules or granules and powders with components B and C and optionally D.

It is also possible to use premixes which have been produced from solutions of the mixture components in suitable solvents, in which case homogenization is optionally effected in solution and the solvent is then removed.

It is possible here to introduce components B and C and optionally D of the composition according to the invention into the polycarbonate by known methods or as a masterbatch. The use of masterbatches is in particular preferable for incorporation of components D, wherein masterbatches based on polycarbonate are used.

In this context, the composition according to the invention can be combined, mixed, homogenized and subsequently extruded in customary apparatus such as screw extruders (TSE twin-screw extruders for example), kneaders or Brabender or Banbury mills. The extrudate can be cooled and comminuted after extrusion. It is also possible to premix individual components and then to add the remaining starting materials individually and/or likewise in a mixture.

It is also possible to combine and mix a premix in the melt in the plastifying unit of an injection-moulding machine. In this case, the melt is converted directly to a shaped body in the subsequent step.

The manufacture of the molded parts from the compositions according to the invention preferably is done by injection-moulding, extrusion or rapid-heatcycle moulding.

Preferably, the compositions according to the invention are used for the manufacturing of injection-moulded parts or extrudates. Injection-moulded parts and extrudates are understood as "moulded parts" according to the invention.

The moulded parts according to the invention preferably are medical technology products or parts of medical technology products, which comprise, or even consist of compositions according to the invention. Parts of medical technology products, which are designated according to the invention, are in particular parts of dialyzers, parts of oxygenators, tubing connectors, miscellaneous connectors, infusion valve connectors, an element for a blood pump, injection syringes, e.g. those of Luer Lock system, an intravenous access component, a two-way valve or selector valve or surgical instruments. Selector valves preferably are three-way valves which are commonly employed in the medical technology sector.

The moulded parts can be those intended for single use as well as those intended for multiple use. Preferably, the moulded parts are intended for single use. In order to avoid infections in patients, it is necessary to also package such parts under sterile conditions. Moulded parts made from the compositions according to the invention can be packaged airtight, sterilized by irradiation and be transported to their place of destination, where the packagings, in particular foil pouches, e.g. laminated foil pouches, e.g. those with an aluminium lamination, are opened immediately before use of the medical technology products or parts of medical technology products. Despite the preceding sterilization, the moulded parts made from polycarbonate material according to the invention do not exhibit any disturbing discoloration (yellowing), which could disturb the impression of "purity" or "sterility".

As radiation, in particular β- or γ-radiation can be used and if both, simultaneously or sequentially for radiation sterilization of the moulded parts according to the invention. The radiation dose preferably is at least 20 kGy, more preferably 25 kGy to 55 kGy, particularly preferably 30 kGy to 50 kGy. Irradiation can take place under oxygen-atmosphere or under oxygen-reduced atmosphere, including an oxygen-free atmosphere.

EXAMPLES

Components:
A1: Makrolon® 2508 from Covestro Deutschland AG. Linear polycarbonate based on bisphenol A having a melt volume flow rate MVR of 15 cm³/10 min (according to DIN EN ISO 1133-1:2012-03), at a test temperature of 300° C. and load 1.2 kg.

B1: Multranol 3600 DHP from Lanxess AG, Germany. Alpha, omega-bis(tetrahydro-2H-pyran-2-yl)-poly[oxy (methyl-1,2-ethanediyl)]. Polyether polyol.

B2: Desmophen® 3600 Z from Covestro Deutschland AG. Bifunctional polyether polyol, based on propylene oxide with propylene glycol as starter. OH number: 56 mg KOH/g. Determined according to DIN 53240-3:2016-03. Most of the hydroxyl end groups are secondary hydroxyl end groups.

$M_n$=2,000 g/mol, determined as described before.

C: 3,3'-thiodipropionic acid from Dr. Spiess Chemische Fabrik GmbH.

D1: pentaerythrityl tetrakis(3-laurylthiopropionate). Songnox® 4120 from Songwon International AG, Switzerland.

D2: mixture of colouring agents.

Procedure:

Laminate pouches (aluminium laminated) for irradiation-sterilization (OPA/Al/PE) from Sudpack Medica, Germany, size: length 24.5 cm*width 15.0 cm, were used. (OPA is a biaxially stretched polyamide film). As oxygen scavengers, those from 02 Zero, UK, were used. For irradiation-sterilization under $O_2$-reduced atmosphere, one FMP (colour sample plate) and 5 pieces oxygen scavenger (50 cc intake capacity) were put into a laminate pouch which was then sealed. For irradiation-sterilization under $O_2$-atmosphere, the FMP alone was sealed in a pouch.

For all examples, FMP with a thickness of 4 mm were used. The compounds according to the examples were produced on an extruder ZE 25 of the company Berstorff with a throughput of 10 kg/h and a rotational speed of 50/min and a temperature of 270° C. The colour sample plates were injection molded on an Arburg ALLROUNDER injection molding machine. Process temperature was 280° C. during injection molding and the mold temperature was 80° C.

As "relaxation time", which the sample had for decoloration (loss of colour) after irradiation, a period of >21 days was used. This period was chosen, as at first, bleaching/decoloration happens slowly, but after a certain period, no further decoloration due to temporary colour centres takes place. Use of the light-proof, aluminium-laminated packagings has an influence on decoloration, as radiation in the VIS range speeds up decoloration.

The irradiation experiments were conducted with β- as well as with γ-radiation with different doses according to DIN EN ISO 11137-1:2015:11. In principle, there is no difference in decoloration of the material after irradiation with β- or γ-radiation.

Radiation used:
1) β-radiation (generation in electron accelerator 10 MeV): high dose rate and limited penetration depth→duration of sterilization process: few seconds
2) γ-radiation (generation by means of $Co^{60}$-source): very high penetration depth and relatively low dose rate→duration of sterilization process: several hours until the intended dose was reached. This was followed by means of a dosimeter.

In case of all compositions according to the invention, no significant plaque formation after irradiation was detectable.

Melt volume flow rate (MVR) was determined as per DIN EN ISO 1133-1:2012-03 (test temperature 300° C., mass 1.2 kg) with a Zwick 4106 apparatus from Zwick Roell after 4 minutes.

Determination of the IMVR-value was made according to DIN EN ISO 1133-1:2012-03 (test temperature 300° C., mass 1.2 kg) with a Zwick 4106 apparatus from Zwick Roell after 19 min.

The Yellowness Index (Y.I.) was determined according to ASTM E 313-15e1 (2015-01-01, observer: 100/illuminant: D65) with sample sheets having a wall thickness of 4 mm measured with a Hunter UltraScanPro device. The difference ΔY.I. between the value 21 days after irradiation and before radiation was formed.

TABLE 1

| | 1V wt.-% | 2V wt.-% | 3 wt.-% | 4 wt.-% | 5 wt.-% | 6V wt.-% | 7V wt.-% | 8V wt.-% | 9V wt.-% |
|---|---|---|---|---|---|---|---|---|---|
| β-sterilization 50 kGy under $O_2$-reduced atmosphere | | | | | | | | | |
| A1 | ≥99.99 | 99.249 | 99.199 | 99.149 | 98.999 | 98.749 | 98.499 | 99.149 | 98.499 |
| B1 | | | | | | | | | |
| B2 | | 0.75 | 0.75 | 0.75 | 0.75 | 0.75 | 0.75 | 0.75 | 0.75 |
| C | | | 0.05 | 0.1 | 0.25 | 0.5 | 0.75 | | |
| D1 | | | | | | | | 0.1 | 0.75 |
| D2 | ≤0.001 | ≤0.001 | ≤0.001 | ≤0.001 | ≤0.001 | ≤0.001 | ≤0.001 | ≤0.001 | ≤0.001 |
| properties | | | | | | | | | |
| MVR | | | 17.5 | 18.2 | 20.2 | 38.8 | 51.6 | | |
| IMVR | | | 19.4 | 21.6 | 26.3 | n.d. | n.d. | | |
| ΔYI (After at least 21 days relaxation-before irradiation) | 53.14 | 20.30 | 13.62 | 12.40 | 11.73 | 10.17 | 10.98 | 16.81 | 14.86 | n.d.: not determinable

V: means comparison example

Unstabilized polycarbonate compositions (1V) show a strong yellowing after radiation with β-radiation. The addition of stabilizers in the form of polyether polyols (2V) already effects a significant reduction of yellowing, but still not satisfying. Already as low amounts as 0.05 wt.-% additional 3,3'-thiodipropionic acid (example 3) effect a remarkable reduction of yellowing, wherein the addition of larger amounts of 3,3'-thiodipropionic acid (examples 4, 5) brings a further improvement. However, even larger amounts, e.g. 0.5 wt.-% und 0.75 wt.-% (6V, 7V) of added 3,3'-thiodipropionic acid lead to such high melt volume rates even before irradiation that processing of such compositions is no longer possible. Known stabilizer pentaerythrityl tetrakis(3-laurylthiopropionate) effects a higher increase in yellowing compared to 3,3'-thidipropionic acid (8V, 9V) compared with examples 4 and 7V.

TABLE 2a

γ-sterilization 30 kGy under O₂ atmosphere

| | 10V wt.-% | 11V wt.-% | 12 wt.-% | 13 wt.-% | 14 wt.-% | 15V wt.-% | 16V wt.-% | 17V wt.-% | 18 wt.-% | 19 wt.-% | 20 wt.-% |
|---|---|---|---|---|---|---|---|---|---|---|---|
| A1 | ≥99.99 | 99.249 | 99.199 | 99.149 | 98.999 | 98.749 | 98.499 | 99.249 | | | |
| B1 | | | | | | | | | 0.75 | 0.75 | 0.75 |
| B2 | | 0.75 | 0.75 | 0.75 | 0.75 | 0.75 | 0.75 | | | | |
| C | | | 0.05 | 0.1 | 0.25 | 0.5 | 0.75 | | 0.05 | 0.1 | 0.25 |
| D2 | ≤0.001 | ≤0.001 | ≤0.001 | ≤0.001 | ≤0.001 | ≤0.001 | ≤0.001 | ≤0.001 | ≤0.001 | ≤0.001 | ≤0.001 |
| Properties | | | | | | | | | | | |
| MVR | | | 17.5 | 18.2 | 20.2 | 38.8 | 51.6 | | 18.3 | 18.5 | 19.6 |
| IMVR | | | 19.4 | 21.6 | 26.3 | n.d. | n.d. | | 20.5 | 22.2 | 26.5 |
| ΔYI (After at least 21 days relaxation-before irradiation) | 16.71 | 11.04 | 8.25 | 6.88 | 6.64 | 7.49 | 8.50 | 8.88 | 7.72 | 6.69 | 5.65 | n.d.: not determinable
V: means comparison example

Also after irradiation with γ-radiation, moulded parts produced from unstabilized polycarbonate compositions (10V) exhibit a significant yellowing, which can already be remarkably reduced by the addition of a polyether polyol (11V, 17V). A further, significant reduction of yellowing can be achieved by the addition of 3,3'-thiodipropionic acid (examples 12-14, 18-20), wherein for amounts of 0.5 wt.-% respectively 0.75 wt.-% (15V, 16V) the melt volume rates are that high that a good processability is not given anymore.

TABLE 2b

γ-sterilization 30 kGy under O₂ atmosphere

| | 21V wt.-% | 22V wt.-% | 23V wt.-% | 24V wt.-% | 25V wt.-% | 26V wt.-% | 27V wt.-% |
|---|---|---|---|---|---|---|---|
| A1 | ≥99.99 | 99.249 | 99.149 | 98.499 | 99.249 | 99.249 | 98.499 |
| B1 | | | | | 0.75 | 0.75 | 0.75 |
| B2 | | 0.75 | 0.75 | 0.75 | | | |
| C | | | | | | | |
| D1 | | | 0.1 | 0.75 | | 0.1 | 0.75 |
| D2 | ≤0.001 | ≤0.001 | ≤0.001 | ≤0.001 | ≤0.001 | ≤0.001 | ≤0.001 |
| Properties | | | | | | | |
| ΔYI (After at least 21 days relaxation-before irradiation) | 16.71 | 11.04 | 11.38 | 10.51 | 8.88 | 10.48 | 9.64 |

The combination of a polyether polyol with a conventional stabilizer, Songnox 4120, effects a reduction of yellowing after irradiation (23V, 24V respectively 26V, 27V compared to 21V or 22V), but the effect is not so pronounced than with the combination of 3,3'thiodipropionic acid (examples 19, respectively 13).

The invention claimed is:

1. A thermoplastic composition consisting of
   A) aromatic polycarbonate,
   B) 0.1 to 5 wt.-% one or more polyether polyols,
   C) 0.01 to 0.30 wt.-% 3,3'-thiodipropionic acid, and
   D) up to 30 wt.-% one or more further additives selected from the group consisting of flame retardants, antidripping agents, impact modifiers, fillers, antistats, colouring agents, pigments, thermal stabilizers different from components B and C, lubricants and/or demoulding agents, UV absorbers, IR absorbers, hydrolysis stabilizers and/or compatibilizer.

2. The thermoplastic composition according to claim 1, wherein the composition comprises 0.05 to 0.30 wt.-% 3,3'-thiodipropionic acid.

3. The thermoplastic composition according to claim 1, wherein the aromatic polycarbonate comprises bisphenol A-based polycarbonate.

4. The thermoplastic composition according to claim 3, wherein the composition does not comprise any other polycarbonate than bisphenol A-based polycarbonate.

5. The thermoplastic composition according to claim 1, comprising at least 95 wt.-% aromatic polycarbonate.

6. The thermoplastic composition according to claim 1, wherein the amount of polyether polyol is 0.1 to 2 wt.-%.

7. The thermoplastic composition according to claim 1, wherein the amount of 3,3'-thiodipropionic acid is 0.05 to 0.25 wt.-%.

8. The thermoplastic composition according to claim 1, consisting of
   A) 69.85 wt.-% to 98.5 wt.-% aromatic polycarbonate,
   B) 0.1 wt.-% to 2 wt.-% polyether polyol,
   C) 0.05 wt.-% to 0.25 wt.-% 3,3 '-thiodipropionic acid and
   D) up to 30 wt.-% one or more further additives selected from the group consisting of flame retardants, antidripping agents, impact modifiers, fillers, antistats, colouring agents, pigments, thermal stabilizers different from components B and C, lubricants, demoulding agents, UV absorbers, IR absorbers, hydrolysis stabilizers and/or compatibilizer.

9. The thermoplastic composition according to claim 1, wherein the polyether polyol is formed from repeating propylene oxide units with propylene glycol as starter molecule and has an OH number within a range of from 50 to 70 mg KOH/g determined according to DIN 53240-3:2016-03.

10. A process for sterilization of moulded parts, wherein a moulded part consisting of or comprising an area consisting of a thermoplastic composition according to claim 1 is exposed to β-radiation and/or γ-radiation with a dose of at least 20 kGy.

11. The process according to claim 10, wherein the irradiation is conducted in an oxygen atmosphere or in oxygen reduced atmosphere.

12. The process according to claim 10, wherein the moulded part is contained in a closed pouch during irradiation.

13. A medical technology product or part of a medical technology product comprising a composition according to claim 1.

14. The medical technology product according to claim 13, wherein the part is a part of a dialyzer, a part of an oxygenator, a tubing connector, a miscellaneous connector, an element for a blood pump, an infusion valve connector, an injection syringe, an intravenous access component, a surgical instrument, or a two-way valve or selector valve.

* * * * *

UNITED STATES PATENT AND TRADEMARK OFFICE
CERTIFICATE OF CORRECTION

PATENT NO. : 11,680,164 B2
APPLICATION NO. : 17/048571
DATED : June 20, 2023
INVENTOR(S) : Wandner et al.

Page 1 of 1

It is certified that error appears in the above-identified patent and that said Letters Patent is hereby corrected as shown below:

On the Title Page

Item (73) Assignee, Please change "Covestro Intellectual Property GMBH &Co. KG" to --Covestro Intellectual Property GMBH &Co. KG, Leverkusen (DE); and Covestro LLC, Pittsburgh, PA (US)--.

Signed and Sealed this
Eighth Day of April, 2025

Coke Morgan Stewart
*Acting Director of the United States Patent and Trademark Office*